US009346867B2

(12) United States Patent
Nishimura et al.

(10) Patent No.: US 9,346,867 B2
(45) Date of Patent: May 24, 2016

(54) CANCER-RELATED GLYCOPEPTIDE EPITOPES, ANTIBODIES AND METHODS OF USE

(75) Inventors: Shin-Ichiro Nishimura, Sapporo (JP); Takahiko Matsushita, Sapporo (JP); Yoshiaki Miura, Glen Rock, NJ (US)

(73) Assignee: Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 13/641,610

(22) PCT Filed: Apr. 15, 2011

(86) PCT No.: PCT/US2011/032716
§ 371 (c)(1),
(2), (4) Date: Oct. 16, 2012

(87) PCT Pub. No.: WO2011/133429
PCT Pub. Date: Oct. 27, 2011

(65) Prior Publication Data
US 2013/0034557 A1    Feb. 7, 2013

Related U.S. Application Data

(60) Provisional application No. 61/325,480, filed on Apr. 19, 2010.

(51) Int. Cl.
| | | |
|---|---|---|
| *C07K 14/47* | (2006.01) | |
| *C07K 16/30* | (2006.01) | |
| *A61P 35/00* | (2006.01) | |
| *A61K 38/16* | (2006.01) | |
| *A61K 38/17* | (2006.01) | |

(52) U.S. Cl.
CPC ......... *C07K 14/4727* (2013.01); *C07K 16/3092* (2013.01); *C07K 2317/21* (2013.01); *C07K 2317/32* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 6,344,203 | B1 | 2/2002 | Sandrin et al. |
| 7,342,094 | B1 | 3/2008 | Karsten et al. |
| 2006/0188996 | A1 | 8/2006 | Nishimura et al. |
| 2007/0014844 | A1 | 1/2007 | Longenecker |
| 2008/0014210 | A1 | 1/2008 | Wreschner et al. |
| 2008/0131495 | A1 | 6/2008 | Longenecker |
| 2009/0004212 | A1 | 1/2009 | Hanisch |
| 2009/0054622 | A1 | 2/2009 | Hanisch et al. |
| 2009/0306291 | A1 | 12/2009 | Shimaoka et al. |
| 2012/0040375 | A1 | 2/2012 | Nishimura et al. |

FOREIGN PATENT DOCUMENTS

| | | |
|---|---|---|
| WO | WO-2004/022590 | 3/2004 |
| WO | WO-2008/011672 | 1/2008 |
| WO | WO 2008011672 | 1/2008 |
| WO | WO-2008/040362 | 4/2008 |
| WO | WO-2010/050528 | 5/2010 |

OTHER PUBLICATIONS

Pudelko et al. (Organic & Biomolecular Chemistry 2006, 4: 713-720).*
Takeuchi et al. (J. Immunol. Methods 270 2002:199-209).*
Dziadek et al. (Aust. J. Chem 2003 56:519-543).*
Astronomo, Rena D. et al., "Carbohydrate vaccines: developing sweet solutions to sticky situations?", *Reviews*, vol. 9 2010, 308-324.
Engelmann, Katja et al., "Indentification and Topology of Variant Sequences within Indivival Repeat Domains of the Human epithelial tumor Mucin MUC1", *The Journal of Biological Chemistry* vol. 276, No. 30 Jul. 27, 2001, 27764-27769.
Gaidzik, Kaiser A. et al., "A synthetic vaccine consisting of a tumor-associated sialyl-T(N)-MUC1 tandem-repeat glycopeptide and tetanus toxoid: induction of a strong and highly selective immune response.", *Angew Chem Int Ed Engl.* 48(41) 2009, Abstract only, 1 pg.
Gendler, Sandra et al., "Preclinical and Clinical Studies of MUC1 Glycopeptide Vaccine Strategies in Breast Cancer", *Women's Cancer Program* 2009, 1 pg.
Hanisch, F. G. , "Design of a MUC1-based cancer vaccine", *The Molecular Biology of Colorectal Cancer* 2005, 705-708.
Hanisch, Franz-Georg et al., "Monoclonal antibody BW835 Defines a Site-specific Thomsen-Friedenreich Disaccharide Linked to Threonine within the VTSA Motif of MUC1 Tandem Repeats", *Cancer Research* Sep. 15, 1995, 4036-4040.
Hirasawa, Yutaka et al., "Natural Autoantibody to MUC1 is a Prognostic Indicatior for Non-Small Cell Lung Cancer", *Am J Respir Crit Care Med* 161 2000, 589-594.
Kinarsky, Leo et al., "Conformational studies on the MUC1 tandem repeat glycopeptides: implication for the enzymatic O-glycosylation of the mucin protein core", *Glycobiology* vol. 13 No. 12 2003, 929-939.
Loveland, Bruce E. et al., "Mannan-MUC1-Pulsed Dendritic Cell Immunotherapy: A Phase I Trial in Patients with Adenocarcinoma", *Clin Cancer Res* 12(3) Feb. 1, 2006, 869-877.
Matsushita, Takahiko et al., "Functional Neoglycopeptides: Synthesis and Characterization of a New Class of MUC1 Glycoprotein Models Havine Core 2-Based O-Glycan and Complex-Type N-Glycan Chains", *Biochemistry* 48 2009, 11117-11133.

(Continued)

*Primary Examiner* — Peter J Reddig
(74) *Attorney, Agent, or Firm* — Servilla Whitney LLC (57) ABSTRACT

Cancer-associated O-glycopeptide combination epitopes derived from the VNTR of MUC1 are disclosed. Autoantibodies present in human sera target the combination epitopes and are reduced or absent in cancer patients. The epitopes are useful as therapeutic and immunoprophylactic cancer vaccines. Monoclonal antibodies directed against the epitopes are also useful as immunotherapeutics for treatment and prevention of cancer. Diagnostic methods using the epitopes and antibodies are also disclosed.

16 Claims, 3 Drawing Sheets

(56) References Cited

OTHER PUBLICATIONS

Mollick, Joseph A. et al., "MUC1-like tandem repeat proteins are broadly immunogenic in cancer patients", *Cancer Immunity* 3:3 Mar. 17, 2003, 1-17.

Mukherkee, P. et al., "MUC1-specific immune therapy generates a strong anti-tumor response in a MUC1-tolerant colon cancer model", *Vaccine* 25(9) Feb. 19, 2007, 1607-1618.

Ohyabu, Naoki et al., "An Essential Epitope of Anti-MUC1 Monoclonal Antibody KL-6 Revealed by Focused Glycopeptide Library", *JACS* 131(47) Nov. 9, 2009, 17102-17109.

Palmer, Martin et al., "Phase I Study of the BLP25 (MUC1 Peptide) Liposomal Vaccine for Active Specific Immunotherapy in Stage IIIB/IV Non-Small-Cell Lung Cancer", *Clinical Lung Cancer* Aug. 2001, 49-57.

Park, Heung K. et al., "MUC1 from he Mucin Family as Potential Tools in Breast Cancer Immunotherapy", *J. of Breast Cancer* 12(3) Sep. 2009, 125-133.

Peat, Nigel et al., "Tissue-specific Expression of a Human Polymorphic Epithelial Mucin (MUC1) in Transgenic Mice", *Cancer Research* 52 Apr. 1, 1992, 1954-1960.

Persson, Jonas et al., "Molecular Evolution of Specific Human Antibody against MUC1 Mucin Results in Improved Recognition of the Antigen on Tumor Cells", *Tumor Biol* 30 (Abstract). 2009, 1 pg.

Ramanathan, RK et al., "Phase I study of a MUC1 vaccine composed of different doses of MUC1 peptide with SP-AS2 adjuvant in resected and locally advanced pancreatic cancer", *Cancer Immunol Immunother* 54(3) Mar. 2005, Abstract only, 1 pg.

Reuschenbach, Miriam et al., "A systematic review of humoral immune responses against tumor antigens", *Cancer Immunol Immunother* 58 2009, 1535-1544.

Rowse, Gerald J. et al., "Tolerance and Immunity to MUC1 in a Human MUC1 Transgenic Murine Model", *Cancer Research* 58 Jan. 15, 1998, 315-321.

Sabbatini, Paul J. et al., "Pilot Study of a Heptavalent Vaccine-Keyhole Limpet Hemocyanin Conjugate plus QS21 in Patients with Peithelial Ovarian Fallopian Tube, or Peritoneal Cancer", *Clinical Cancer Res* 12(14) Jul. 15, 2007, 4170-4177.

Sangha, Randeep et al., "L-BLP25: A Peptide Vaccine Strategy in Non-Small Cell Lung Cancer", *Clin Cancer Res* 13(15 Suppl) Aug. 1, 2007, 4652s-4654s.

Sorensen, Anne L. et al., "Chemoenzymatically synthesized multimeric Tn/STn MUC1 glycopeptides elicit cancer-specific anti-MUC1 antibody responses and override tolerance", *Glycobiology* 16(2) 2006, 96-107.

Stepensky, D. et al., "O-glycosylated versus non-glycosylated MUC1-derived peptides as potential targets for cytotoxic immunotherapy of carinoma", *Clinical and Experimental Immunology* 143 2005, 139-149.

Tarp, Mads A. et al., "Identification of a novel cancer-specific immunodominant glycopeptide epitope in the MUC1 tandem repeat", *Glycobiology* 17(2) 2007, 197-209.

Von Mensdorff-Pouilly, Silvia et al., "Sequence-variant repeats of MUC1 show higher conformational flexibility, are less densely O-glycosylated and induce differential B lymphocyte responses", *Glycobiology* 15(8) 2005, 735-746.

Von Mensdorff-Pouilly, S. et al., "Survival in Early Breast Cancer Patients is Favorably Influenced by a Natural Humoral Immune Response to Polymorphic Epithelial Mucin", *Journal of Clinical Oncology*, vol. 18, No. 3 2000, 574-583.

Wandall, Hans H. et al., "Cancer Biomarkers Defined by Autoantibody Signatures to Aberrant O-Glycopeptide Epitopes", *Cancer Research* 70(4) Feb. 15, 2010, 1306-1313 and Supplemental Data.

Wilkinson, RW et al., "A transgenic mouse model for tumor immunotherapy: induction of an anti-idiotype response to human MUC1", *British Journal of Cancer* 83(9) 2000, 1202-1208.

PCT International Search Report and Written Opinion in PCT/US2011/032716, mailed Jul. 6, 2011, 13 pgs.

Bhavanandan, V.P. et al., "Purification and characterization of the MUC1 mucin-type glycoprotein, epitectin, from human urine: structures of the major oligosaccharide alditols", *Glycoconjugate Journal*, vol. 15 1998, pp. 37-49.

George, Shaji K. et al., "Chemoenzymatic Synthesis of Sialylated Glycopeptides Derived from Mucins and T-Cell Stimulating Peptides", *JACS*, vol. 123, No. 45 Nov. 14, 2001, pp. 11117-11125.

\* cited by examiner

Fig. 1

Epitope 1 expressed on SEQ ID NO:3

Ser-Thr-Ala-Pro-Pro-Ala-His-Gly-Val-Thr-Ser-Ala-Pro-Asp-Thr-Arg-Pro-Ala-Pro-Gly

SEQ ID NO:1

Epitope 2 expressed on SEQ ID NO:4

Gly-Val-Thr-Ser-Ala-Pro-Asp-Thr-Arg-Pro-Ala-Pro-Gly-Ser-Thr-Ala-Pro-Pro-Ala-His

SEQ ID NO:2

Fig. 2

CANCER-RELATED GLYCOPEPTIDE EPITOPES, ANTIBODIES AND METHODS OF USE

CROSS REFERENCE TO RELATED APPLICATIONS

This application is the National Phase entry of PCT/US2011/032716, filed Apr. 15, 2011, which claims the benefit under 35 USC 119(e) of U.S. Provisional Application 61/325,480, filed Apr. 19, 2010, the contents of which are incorporated herein by reference in their entirety.

TECHNICAL FIELD

The present invention relates to glycopeptides. In particular, the invention includes glycopeptide epitopes derived from mucin 1 (MUC1), antibodies targeting the glycopeptide epitopes and use of the epitopes and antibodies in therapeutic and diagnostic methods.

REFERENCE TO SEQUENCE LISTING

The material contained in the text file identified as "EZS0008-00P1 Sequence Listing_ST25.txt" (created Apr. 13, 2010; 1,248 bytes) is hereby incorporated by reference.

REFERENCE TO SEQUENCE LISTING

The material contained in the text file identified as "EZS0008-00WO Sequence Listing_ST25.txt" (created Apr. 14, 2011, 1,248 bytes) is hereby incorporated by reference.

BACKGROUND

Mucin 1 (MUC1) is a highly O-glycosylated protein normally expressed on epithelial, endothelial and other normal cell types. MUC1 and other members of the mucin family provide lubrication of cell surfaces and serve as a barrier to physical and biological assaults on the cell. However, in human tumors mucins are often aberrantly expressed. This is believed to contribute to tumor progression by altering the surface properties of tumor cells. MUC1 is one of the best characterized of the mucins. It has a role in cell adhesion and has been shown to interact with various signaling proteins involved in cellular growth.

MUC1 has been exclusively localized to the apical surfaces of normal epithelial cells of breast, salivary gland and lung. The protein backbone has both highly glycosylated regions and unglycosylated regions. The protein core exhibits of a variable number of tandem repeats (VNTR) each 20 amino acids in length. The carbohydrate side chains are attached by an α-linkage between N-acetylgalactosamine and the oxygen atom of serine or threonine. Each VNTR contains five potential sites for glycosylation.

Humans are generally immunologically tolerant to the human MUC1 protein core and its normal glycoforms. However, MUC1 is up-regulated in many malignant tumors. In addition, cancer-associated MUC1 is underglycosylated (i.e., hypoglycosylated) and exhibits an abnormal number of truncated immature O-glycan side-chains. The changes in the carbohydrate structure of cancer-associate MUC1 distinguish it structurally from MUC1 found in normal tissues. As a consequence of hypoglycosylation, regions of the protein backbone that are normally masked by carbohydrate become exposed, making the cancer-associate molecule antigenically distinct from the MUC1 found in normal epithelia.

Because MUC1 is over-expressed in many cancers, it has been used as a serum marker for detecting recurrence or prognosis in cancer patients, particularly breast cancer patients. The MUC1 glycoforms associated with normal breast epithelial cells are core 2 glycoforms that are characterized by branching at the 6-position of the GalNAc residue. In contrast, in breast cancer core 1 glycoforms predominate. Core 1 glycoforms are characterized by a lack of branching at the 6-position of GalNAc. The failure of breast cancer cells to produce normally branched glycoforms may be due to a decrease in expression of core2β 6-GlcNAc transferase (C2GnT1). Anti-MUC1 antibodies have also been employed as immunohistochemical markers in the diagnosis of such cancers. Anti-MUC1 antibodies directed against different regions of MUC1, including the VNTR, are known.

Cellular immune responses to MUC1 have been extensively characterized in cancer patients. Humoral immune responses to MUC1 in malignancy have also been reported and correlated with improved outcome in breast cancer. There is therefore interest in developing antibodies to MUC1 and immunogens based on the MUC1 polypeptide for use in immunotherapy for patients with cancer for use in treating tumors expressing the MUC1 antigen. It is also of interest to elicit cellular and humoral immune responses directed specifically to cancer-associated glycoforms of MUC1 to improve the therapeutic effect.

The heptapeptide sequence Pro-Asp-Thr-Arg-Pro-Ala-Pro (PDTRPAP, SEQ ID NO:1) is derived from the VNTR of MUC1 and has been identified as the epitope recognized by anti-KL-6 monoclonal antibody (anti-KL-6MAb). Ohyabu, N. J., et al. *Am. Chem. Soc.* 2009; 131(47):17102-9. The threonine residue of this epitope is modified by Neu5Ac alpha 2,3 Gal beta 1,3 GalNAc alpha (2,3 sialyl T antigen or "23ST", a core 1-type O-glycan). The authors report that the antibody is not specific for this epitope structure, and that it reacts with various kinds of tumor-derived MUC1 glycoproteins as well as the glycoprotein biomarker associated with interstitial pneumonia. Further, glycosylation of threonine/serine residues outside the epitope strongly influenced the antibody/epitope interaction.

Two glycoforms of the tetrapeptide GSTA (SEQ ID NO:2) with GalNAcα1-O-Ser/Thr (Tn) and NeuAcα2-6Gal-NAcα1-O-Ser/Thr (sialyl-Tn or STn) O-glycosylation have also been reported as a cancer-specific immunodominant epitope found in the VNTR. Tarp, M. A., et al. *Glycobiology* 2007; 17(2):197-209. Vaccines based on this glycopeptide were capable of overriding tolerance in human MUC1 transgenic mice and induced humoral immunity. Sorensen, A. L., et al. *Glycobiology* 2006; 16:96-107.

In addition, autoantibodies directed to MUC1 have been reported in healthy persons and in patients with lung cancer; however, the levels in lung cancer patients were significantly lower than those in normal individuals. Hirasawa, Y, et al. *Am. J. Respir. Crit. Care Med.* 2000; 161:589-594. These authors also reported that the one-year survival rate of patients with higher concentrations of autoantibody was significantly higher than that of patients with lower levels of autoantibody and suggested that the degree of decrease in autoantibody level may be associated with a patient's prognosis. Autoantibodies in breast cancer patients that are indicators of the outcome of disease have also been reported by von Mensdorff-Pouilly, S., et al. *J. Clin. Oncology* 2000; 18(3):574-583. In this study, detection of the antibodies in pretreatment sera had significant prognostic value and was associated with significant benefit in survival, suggesting that vaccination of patients with MUC1-derived (glyco)peptides may influence the outcome of disease. However, in this study, the authors reported that the levels of antibody were significantly higher in the breast cancer group and the benign breast tumor group than in healthy women.

Autoantibodies to aberrant O-glycopeptide epitopes are therefore of interest as biomarkers for detection of cancer. Based on a failure in one study to detect IgG autoantibodies to peptide epitopes in human sera, it has been suggested that autoantibody biomarker discovery strategies should be directed to the cancer-associated aberrant posttranslational modifications of MUC1. Such "O-glycopeptide combination epitopes" include both the peptide backbone and the cancer-associated posttranslational modification hapten structure. Wandall, H., et al. *Cancer Res* 2010; 70(4):1306-13. Although the aberrantly glycosylated O-glycopeptidome of MUC1 has great potential as a source of targets for cancer-associated autoantibodies, there are thousands of distinct MUC1-derived O-glycoproteins that may be combined with numerous distinct aberrant O-glycan structures, any of which may or may not prove to be useful targets for autoantibody-based detection of cancer. Such discovery is further complicated by the presence in sera of natural antibodies to cancer-associated truncated carbohydrate haptens. There continues to be a need for discovery of additional MUC1-derived O-glycopeptide combination epitopes and larger glycopeptides containing such epitopes for use as therapeutic cancer vaccines and for generating specific therapeutic antibodies. Such O-glycopeptide combination epitopes and antibodies targeting them are also desirable for use in diagnostic and prognostic assays for evaluation of the presence or risk of cancer. The invention disclosed herein meets these needs.

SUMMARY

The present invention provides cancer-associated O-glycopeptide combination epitopes derived from the VNTR of MUC1. Specifically, the glycosylation of these epitopes is limited to 2,3 sialyl-T (23ST) at a single threonine residue. The epitopes may, however, be contained within larger peptides as necessary to improve immunogenicity or for other purposes. The epitopes are the targets of autoantibodies in human sera. Autoantibodies directed against the epitopes of the invention are present at high levels in healthy individuals but are reduced or absent in cancer patients. These epitopes are therefore believed to play an important role in preventing development of cancer in humans by eliciting production of the autoantibodies in healthy individuals. The reduction in the level of serum autoantibody directed to the combination epitopes is associated with many types of cancer, but is particularly associated with breast and colon malignancy.

The O-glycopeptide combination epitopes and larger peptides containing them are useful in therapeutic compositions for treating cancer by eliciting a humoral immune response. The O-glycopeptide combination epitopes and larger peptides containing them are also useful in diagnostic compositions for determining the level of autoantibody in human biological samples as an indicator of the prognosis of cancer patients, for evaluating the risk of developing cancer in healthy individuals and as an indicator of the presence or absence of cancer (i.e., cancer diagnosis). Further, monitoring the generation of specific autoantibodies to these epitopes provides a method for evaluating the efficacy of vaccine treatment employing the combination epitopes. The O-glycopeptide combination epitopes are also useful for generation of polyclonal antibodies directed against the combination epitopes and hybridomas producing monoclonal antibodies that are specific for the 23ST-glycopeptide combination epitopes. Monoclonal antibodies specifically directed against the 23ST-glycopeptide combination epitope are useful in therapeutic compositions for treating cancer and in immunoprophylactic compositions for reducing the risk of developing cancer. Such monoclonal antibody compositions are administered to an individual with reduced levels of serum autoantibodies in order to raise the level of antibodies in the blood that are reactive to the O-glycopeptide combination epitopes to at least normal levels, preferably above normal levels.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Figure 1:
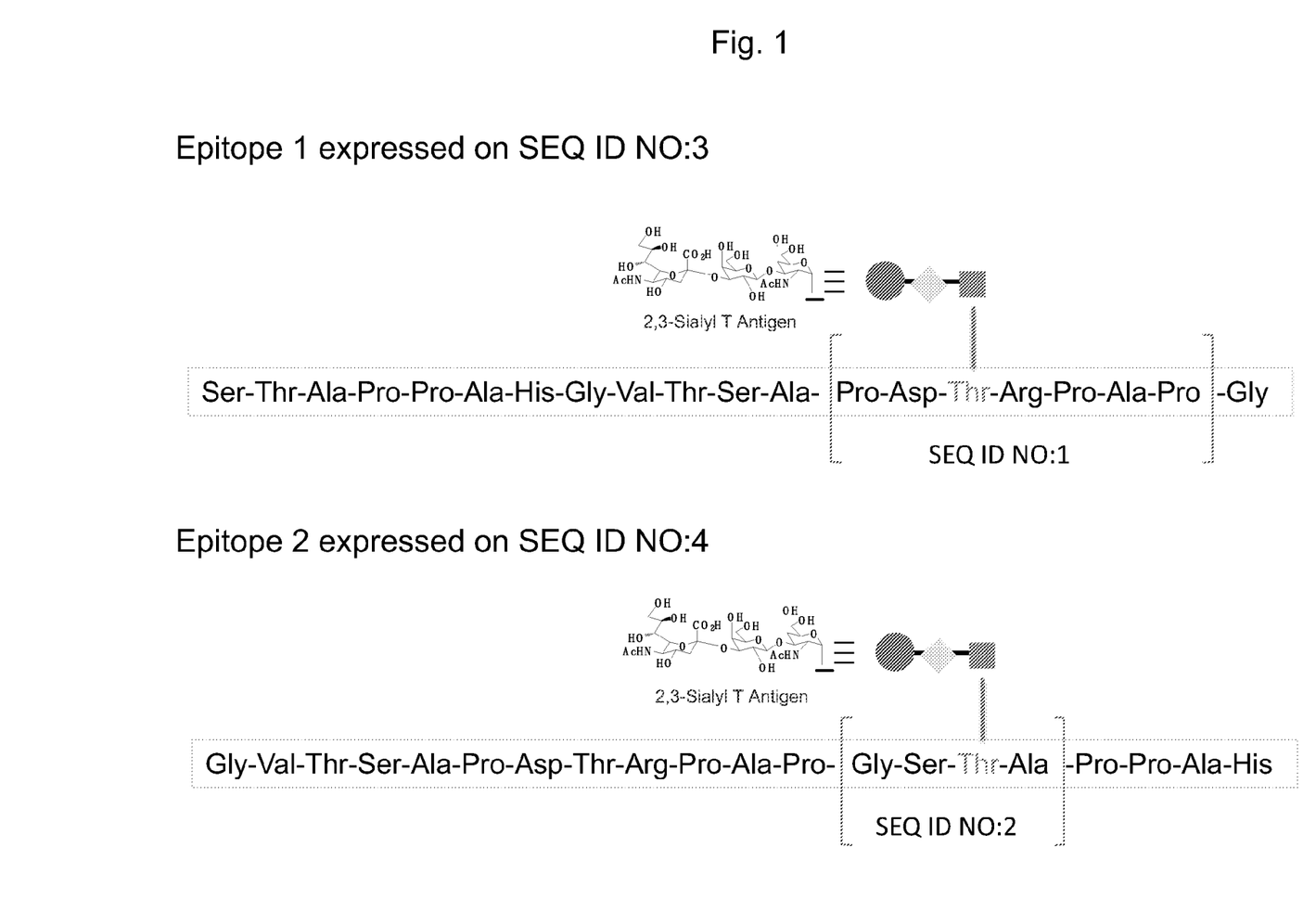
FIG. 1 describes the structure of the two combination epitopes.

As used herein, the term SEQ ID NO:3 (T15-23ST) refers to the amino acid sequence of SEQ ID NO:3 including 23ST glycosylation at the position-15 threonine. Similarly, the term SEQ ID NO:4 (T15-23ST) refers to the amino acid sequence of SEQ ID NO:4 including 23ST glycosylation at the position-15 threonine. The structures of SEQ ID NO:3 (T15-23ST) and SEQ ID NO:4 (T15-23ST) are illustrated in FIG. 1.

As used herein, the term SEQ ID NO:1 (T3-23ST) refers to the amino acid sequence of SEQ ID NO:1 including 23ST glycosylation at the position-3 threonine. Similarly, the term SEQ ID NO:2 (T3-23ST) refers to the amino acid sequence of SEQ ID NO:2 including 23ST glycosylation at the position-3 threonine. The structures of SEQ ID NO:1 (T3-23ST) and SEQ ID NO:2 (T3-23ST) are illustrated in FIG. 1.

As used herein, the term "combination epitope" with respect to the glycopeptides of the invention refers to an antigenic or immunogenic epitope defined by both its peptide sequence and a glycan linked to the peptide sequence. That is, antibodies which specifically bind the combination epitope recognize both the peptide and glycan portions of the epitope. Such antibodies do not bind substantially to either the peptide portion or the glycan portion of the epitope alone.

As used herein, the term "serum" refers to the liquid separated from clotted blood and the term "plasma" refers to the liquid separated from blood without clotting. Both serum and plasma have the cellular components of blood removed but contain a variety of proteins, including immunoglobulins (antibodies). Therefore, "serum" and "plasma" are used interchangeably when referring to the methods and compositions of the invention and use of one term is intended to include the other.

As used herein, the phrases "treating cancer" and "treatment of cancer" mean to inhibit the replication of cancer cells, inhibit the spread of cancer, decrease tumor size, lessen or reduce the number of cancerous cells in the body, or ameliorate or alleviate the symptoms of the disease caused by the cancer. The treatment is considered therapeutic if there is a decrease in mortality and/or morbidity, or there is a decrease in disease burden as may be manifested by reduced numbers of malignant cells in the body or decreased tumor size.

As used herein, the term "immunotherapy" and its equivalents refer to treatment of an individual for the purpose of increasing immunity to a cancer. Immunotherapy may comprise treatment with either a therapeutic vaccine or antibody replacement, or both.

As used herein, the term "therapeutic vaccine" and its equivalents, with respect to methods and compositions, refers to treatment of an individual who has cancer wherein immunogenic molecules intended to elicit an immune response against the cancer are administered to the individual.

As used herein, the term "antibody replacement" and its equivalents, with respect to methods and composition, refers to treatment of an individual who has cancer or to immunopropylactic methods for prevention of cancer wherein antibody is administered to the individual for the purpose of increasing the amount of antibody in the circulation targeting cancer cells.

As used herein, the term "immunoprophylaxis," "immunoprophylactic" and their equivalents, with respect to methods and compositions, refers to treatment of an individual who is not known to have cancer but for whom it is desired to increase immunity to cancer for the intended purpose of preventing the cancer. Immunoprophylaxis may be carried out by administration of immunogenic compositions or by antibody replacement.

A first cancer-associated combination epitope of MUC1 comprises SEQ ID NO:1 (PDTRPAP) with 23ST O-glycosylation on the T residue. The first combination epitope may be contained in a larger peptide sequence, particularly when used as a therapeutic vaccine or for immunoprophylaxis, and in that case there is preferably no additional glycosylation outside of the combination epitope sequence. For example, the first combination epitope may be present in a peptide having the following amino acid sequence: STAPPAH-GVTSA<u>PDTRPAP</u>GSTA (SEQ ID NO:3).

A second cancer-associated combination epitope of MUC1 comprises SEQ ID NO:2 (GSTA) with 23ST O-glycosylation on the T residue. The second combination epitope may be contained in a larger peptide sequence, particularly when used as a therapeutic vaccine or for immunoprophylaxis, and in that case there is preferably no additional glycosylation outside of the combination epitope sequence. For example, the second combination epitope may be present in a peptide having the following amino acid sequence: GVTSAPDTR-PAP<u>GSTA</u>PPAHGVT (SEQ ID NO:4).

The first and second combination epitopes described above were discovered in a synthetic combinatorial library of MUC1 glycopeptides derivatives having various carbohydrate core structures. The library was created at Hokkaido University using the chemoenzymatic synthesis methods of Matsushita, T., et al. (*Biochemistry* 2009; 48: 11117-11133).

Microarray slides were printed with the MUC1 glycopeptide library for use in screening against human sera. Sera were obtained from healthy individuals and from cancer patients (representing colon, breast and kidney cancers) and serially diluted from 25- to 800-fold for use in the microarray analysis.

The glycopeptide arrays were prepared and analyzed as follows:

Reagents: Reaction buffer (50 mM Tris-HCl, pH 7.4, containing 100 mM NaCl, 1 mM CaCl2, 1 mM MnCl, 1 mM MgCl2, 0/05% Tween 20); wash buffer (reaction buffer containing 0.05% Triton X-100 instead of Tween 20); secondary antibody (Cy5-conjugated Affinipure F(ab') 2 fragments, IgG+IgM (H+L) goat anti-human from Jackson Immunoresearch, #109-176-127).

Prior to use, the secondary antibody was rehydrated with 0.75 ml Milli-Q water and diluted 1:100 with reaction buffer.

The microarray reader was an Axon GenePix 4300A from MDS Analytical Technologies using GenePix Pro 7 software.

Methods:
1. Serially dilute sera from 25 to 800-fold.
2. Set the Microarray slide in SIMprex 64 Multi-Array Device (Gentel Biosciences, #4-1029) with SIMprex Gasket (Gentel Biosciences, #4-1026).
3. Apply 100 μl of the diluted sera to the wells of the device.
4. Cover with SIMprex Well Seal (Gentel Biosciences, #4-1027).
5. Incubate for 2 hours at room temperature.
6. Remove liquid from the device by gently pipeting.
7. Apply 100 μl of the wash buffer to each well during 1 minute.
8. Remove liquid from the device by gently pipeting.
9. Repeat 7) and 8) one additional time.
10. Apply 100 μl of the diluted secondary antibody to the wells.
11. Cover with the well seal.
12. Incubate for 1 hour at room temperature.
13. Remove liquid from the device.
14. Remove the slide from the device and wash the slide with wash buffer.
15. Wash the slide with Milli-Q water.
16. Dry the slide by centrifugation.
17. Scan the slide using GenePix 4300A.

Using these methods SEQ ID NO:3 (T15-23ST) and SEQ ID NO:4 (T15-23ST) were identified in the glycopeptide library as positive in reactions with normal sera and negative or having reduced reactivity with sera from cancer patients. Binding of autoantibodies in sera to SEQ ID NO:3 or SEQ ID NO:4 amino acid sequences having various O-glycosylation patterns was evaluated using an experimental protocol similar to the one described above. The glycoforms tested and the results are shown in the following Tables:

TABLE 1

SEQ ID NO: 4

| Glycoform | Position in Peptide | Autoantibody Binding |
|---|---|---|
| naked | N/A | Neg. |
| Tn | T-8 | Neg. |
| Tn | S-14 | Neg. |
| Tn | T-15 | Neg. |
| T | T-8 | Neg. |
| T | S-14 | Neg. |
| T | T-15 | Neg. |
| 23ST | T-8 | Neg. |
| 23ST | S-14 | Neg. |
| 23ST | T-15 | Pos. |

TABLE 2

SEQ ID NO: 3

| Glycoform | Position in Peptide | Autoantibody Binding |
|---|---|---|
| Naked | N/A | Neg. |
| Tn | T-10 | Neg. |
| Tn | S-11 | Neg. |

TABLE 2-continued

SEQ ID NO: 3

| Glycoform | Position in Peptide | Autoantibody Binding |
|---|---|---|
| Tn | T-15 | Neg. |
| T | T-10 | Neg. |
| T | S-11 | Neg. |
| T | T-15 | Neg. |
| 23ST | T-10 | Neg. |
| 23ST | S-11 | Neg. |
| 23ST | T-15 | Pos. |

Autoantibodies in the sera of healthy individuals did not bind to the SEQ ID NO:3 or SEQ ID NO:4 amino acid sequences with O-glycosylation patterns other than 23ST at T-15. It was observed that autoantibody binding was negative for 23ST at T-8 of SEQ ID NO:4 in spite of the fact that T-8 of SEQ ID NO:4 is contained in an amino acid sequence that is the same as SEQ ID NO:1. However, the glycopeptides were linked to the microarray plate via 5-oxo linkages at the N-terminus. The position of SEQ ID NO:1 in SEQ ID NO:4 is close to this linkage, so it is likely that this configuration prevented antibody access to the epitope. In contrast, the position of SEQ ID NO:1 in SEQ ID NO:3 is distanced from the linkage point and was therefore accessible for autoantibody binding. The autoantibodies were therefore determined to be specific for SEQ ID NO:3 and SEQ ID NO:4 peptides having only 23ST-glycosylation at the T-15 amino acid residue.

Figure 2:
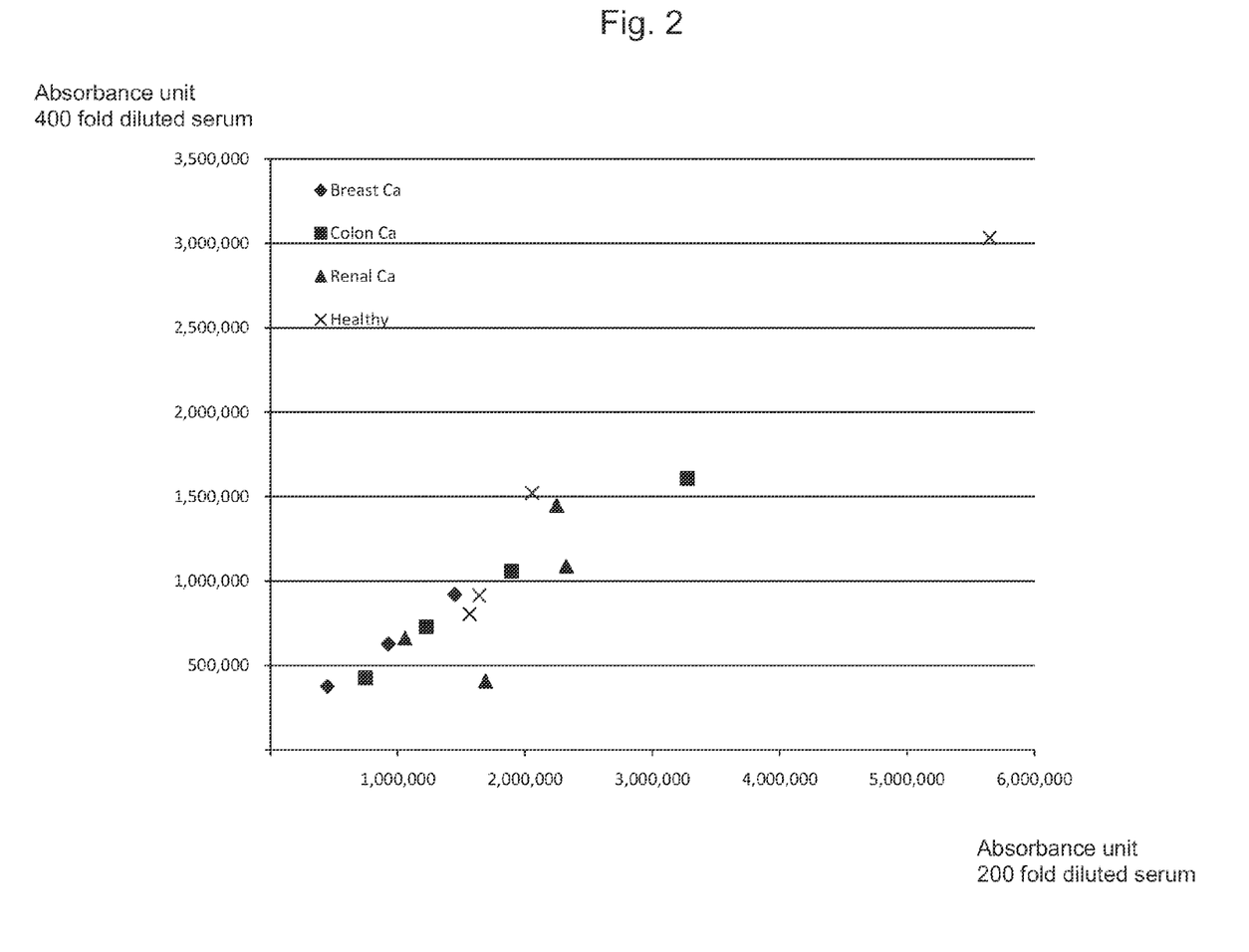
FIG. 2 illustrates the association of SEQ ID NO:3 (T15-23ST) autoantibody level with the presence or absence of cancer.
Figure 3:
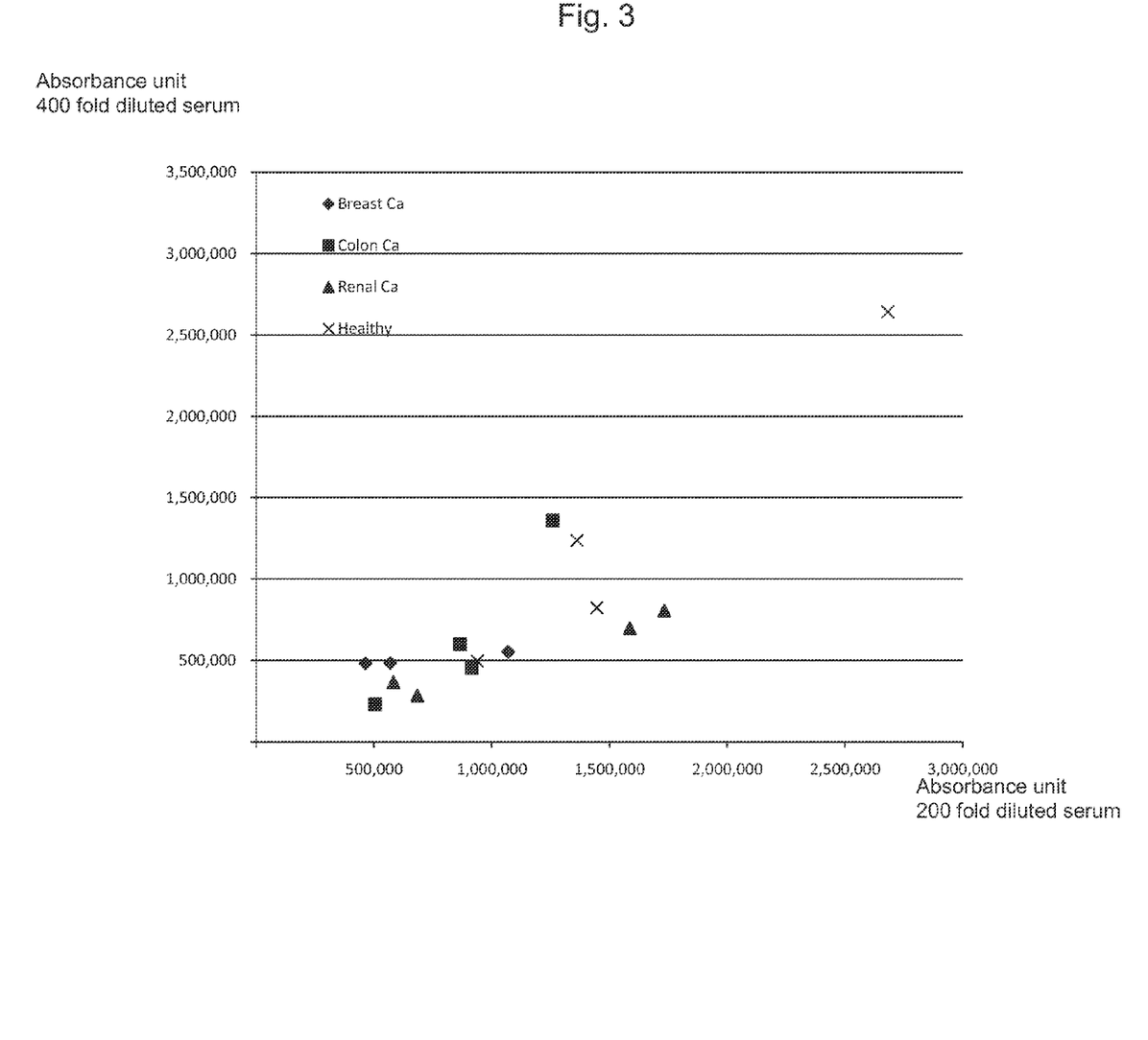
FIG. 3 illustrates the association of SEQ ID NO:4 (T15-23ST) autoantibody level with the presence or absence of cancer.

In addition, the autoantibodies were found to be present at higher levels in normal healthy individuals than in cancer patients. Specifically, autoantibodies were reduced or absent in cancer patients as compared to normal healthy individuals. Absorbance data were plotted as 200-fold serum dilution vs. 400-fold serum dilution for each of SEQ ID NO:3 (T15-23ST) and SEQ ID NO:4 (T15-23ST) to evaluate the degree of association of autoantibody level with disease. For both glycopeptides the plot was substantially linear and revealed a trend toward higher values (i.e., higher autoantibody levels) in normal healthy individuals as compared to cancer patients (FIG. 2 and FIG. 3). In general, absorbance values for healthy individuals were equal to or greater than about 1 million absorbance units (AU), whereas absorbance values for breast and colon cancer patients were equal to or less than about 1 million AU. Results for renal cancer patients were substantially more variable, with two patients falling well into the range of normal. Values for renal cancer ranged from about 600 thousand to 1.75 million AU.

The range of normal values for autoantibodies directed to SEQ ID NO:3 (T15-23ST) and SEQ ID NO:4 (T15-23ST) is therefore typically greater than about 1 million AU, for example from about 1,000,100 AU to about 2.7 million AU, from about 1,000,100 AU to about 1.5 million AU or from about 1.25 million AU to about 1.5 million AU. The range of values indicating the disease state is typically about 1 million AU or less, for example from about 500 thousand AU to about 1 million AU, from about 50 thousand AU to about 500 thousand AU or from about 250 thousand AU to about 900 thousand AU. Autoantibodies may also be essentially undetectable in this assay in the disease state. While these data might suggest that the reduction in autoantibodies may be more reliably predictive for breast and colon cancer than renal cancer, the greater variability in renal cancer patients may also be due to the small sample size in this study.

The combination epitopes disclosed herein are specifically recognized by autoantibodies that are reduced or absent in patients with cancer. As such, the change in autoantibody level is believed to be an early indicator of disease. One aspect of the present invention therefore relates to use of the combination epitopes in diagnostic assays and methods for detection of cancer. For example, they may be used (alone or within larger peptide sequences as exemplified by SEQ ID NO:3 (T15-23ST) and SEQ ID NO:4 (T15-23ST)) as targets in diagnostic ELISA assays similar to those described above. Absorbance readings indicate the level of autoantibody present in the individual's serum as described above and are indicative of the presence or absence of cancer. Adaptation of the invention to other known assay methods suitable for determining antibody levels in serum is within the ordinary skill in the art. For example, autoantibody titers may be determined as described by Engvall, E., et al. (*Immunochemistry* 1971; 9(8):871-4. "Enzyme-linked immunosorbent assay (ELISA). Quantitative assay of immunoglobulin G"). Alternatively, other known antibody quantitation methods suitable for clinical use may be used to determine the level of the autoantibodies described herein. For example, as described in "Antibodies: A Laboratory Manual by Ed Harlow and David Lane. By determining the range of autoantibody titers in normal serum and the range of autoantibody titers in the sera of cancer patients, the range of autoantibody titers that is indicative of the presence of cancer can be statistically determined. As described above for ELISA assays, autoantibody titers that are reduced in comparison to normal titers indicate the presence of cancer in the patient, especially in the case where MUC1 23ST epitopes are present in the serum or tissue.

The assays described above using the combination epitopes disclosed herein are also useful for determining the prognosis of a cancer patient. In this case, the subnormal ranges of autoantibody are indicative of a relatively poor prognosis, with lower subnormal results being indicative of a worse prognosis than higher subnormal results. In contrast, cancer patients having normal levels of autoantibody will generally be evaluated as having a good prognosis.

The assays described above using the combination epitopes disclosed herein are also useful in assays for determining an individual's level of risk for developing cancer (including risk of cancer recurrence) and for monitoring changes in cancer risk over time. It is believed that the autoantibodies described herein contribute to immune surveillance against MUC1-expressing cancer cells. That is, normal or high levels of circulating autoantibody are protective but reduced levels of circulating autoantibody may be inadequate to recognize and remove malignant cells as they arise. In this case, the subnormal ranges of autoantibody are indicative of a relatively higher cancer risk, with lower subnormal results being indicative of a greater risk than higher subnormal results. Individuals having autoantibody levels in the normal range generally will be evaluated as having a normal risk of developing cancer and individuals having autoantibody levels in the high normal range will be evaluated as having particularly high resistance to developing cancer. For monitoring changes in the level of activity of the anti-cancer immune surveillance system of an individual over time, a baseline titer for the autoantibodies is established for the individual. Subsequent testing will detect increases or decreases relative to the baseline titer, wherein increasing values indicate decreasing cancer risk and decreasing values indicate increasing cancer risk.

In yet another embodiment, the assays described above may be used to monitor the efficacy of cancer therapy Because it has been found that autoantibodies directed against the combination epitopes are reduced and may even be substantially absent in patients with cancer, in one aspect the present invention is directed to an immunotherapeutic method of inducing a cancer specific immune response toward the combination epitopes, the method comprising immunizing a human cancer patient with an immunogenic glycopeptide comprising the combination epitopes described herein. While such therapeutic immunization or vaccination will be effective against any cancer which expresses MUC1 having the SEQ ID NO:1 (T3-23ST) or SEQ ID NO:2 (T3-23ST) combination epitope, in a preferred embodiment the immunotherapeutic method is for treatment of breast cancer, colon cancer or renal cancer. In a specific example, therapeutic vaccination may be accomplished by administration of SEQ ID NO:3 (T15-23ST) or SEQ ID NO:4 (T15-23ST) to an individual in need thereof. Desirably, the specific immune response will be a humoral response that mimics the autoantibodies found in healthy individuals. Exposure of the patient to either or both of the combination epitopes (each alone or within a larger peptide sequence) will elicit a humoral immune response, increasing the level of autoantibody and thereby increasing the patient's natural immunity to the abnormal glycopeptides associated with cancer. Ideally, treatment with a combination epitope as disclosed herein will increase the level of autoantibody to at least the minimum normal level (such as 1 million AU or greater in ELISA) or to near-normal levels (80-99%, such as 800 thousand AU-999 thousand AU in ELISA). Preferably, treatment with a combination epitope as disclosed herein will increase the level of autoantibody to at least 60% of the minimum normal level (such as 600 thousand AU or greater in ELISA) or to 60-80% of the minimum normal level (such as 600 thousand AU-800 thousand AU in ELISA). However, use of the therapeutic vaccine will more preferably increase the level of autoantibodies to at least 110% of the minimum normal level (such as at least 1.1 million AU in ELISA), 110-125% of the minimum normal level (such as 1.1 million AU-1.25 million AU in ELISA), 125-150% of the minimum normal level (such as 1.25 million AU-1.50 million AU in ELISA) or 150-250% of the minimum normal level (1.50 million AU-2.50 million AU in ELISA).

Therapeutic vaccine compositions comprising the combination epitopes of the invention are also contemplated by the present invention. In a preferred embodiment, the therapeutic vaccine composition is a cancer vaccine for treatment of breast cancer, colon cancer, renal cancer or other cancers which express MUC1 having the SEQ ID NO:1 (T3-23ST) and/or SEQ ID NO:2 (T3-23ST) combination epitopes. The composition may comprise a peptide containing the combination epitope(s) and at least one pharmaceutically acceptable excipient. For use as a therapeutic vaccine, the composition will typically be in the form of an injectable composition such as a solution, suspension or emulsion incorporating a peptide containing the combination epitope and a liquid excipient (e.g., saline, water, phosphate or carbonate buffer, propylene glycol, sorbitol, sucrose, etc.). To increase the immunogenicity of the vaccine, the peptide containing the combination epitope may be conjugated to a suitable carrier, such as human serum albumin (HSA), Keyhole limpet hemocyanin (KLH), influenza hemagglutinin, cholera toxin, tetanus toxoid, heat shock protein 65 (HSP65), or other carriers known in the art.

Peptides containing the combination epitopes of the invention for use in the foregoing methods and compositions may be produced by chemoenzymatic synthesis methods known in the art, for example peptide synthesis followed by glycosylation and sialylation of the peptide in vitro using purified recombinant glycosyltransferases and sialyltransferases. See, e.g., Matsushita, T., et al. *Biochemistry* 2009; 48:11117-11133 ("*Functional neoglycopeptides: Synthesis and characterization of new class MUC1 glycoprotein models having core 2-based O-glycan and complex-type N-glycan chains*"). Alternatively, the desired peptide sequence may be produced using known recombinant DNA techniques to express the peptide, followed by enzymatic glycosylation and sialylation of the purified peptide.

In addition, one aspect of the invention contemplates monoclonal antibodies specific for a combination epitope according to the invention. Such monoclonal antibodies may be produced according to methods known in the art, and are useful as immunotherapeutics for administration to cancer patients to treat the disease by increasing the level of antibodies specifically targeting the cancer-associated combination epitope. This therapeutic approach provides antibody replacement therapy for the naturally occurring autoantibodies that are reduced or absent in cancer patients. Ideally, such immunotherapy will increase the combination epitope-directed antibody level in the serum to at least the minimum normal level of autoantibodies (such as 1 million AU or greater in ELISA) or to near-normal levels (80-99%, such as 800K AU-999K AU in ELISA). Preferably, the immunotherapy will increase the level of serum antibody to at least 60% of the minimum normal level of autoantibodies (such as 600K AU or greater in ELISA) or to 60-80% of the minimum normal level (such as 600K AU-800K AU in ELISA). However, use of the monoclonal antibody for immunotherapy will more preferably increase the level of combination epitope-directed antibodies in the serum to at least 110% of the minimum normal level of autoantibodies (such as at least 1.1 million AU in ELISA), 110-125% of the minimum normal level (such as 1.1 million AU-1.25 million AU in ELISA), 125-150% of the minimum normal level (such as 1.25 million AU-1.50 million AU in ELISA) or 150-250% of the minimum normal level (1.50 million AU-2.50 million AU in ELISA). By increasing the level of circulating antibody directed against a combination epitope of the invention, the patient's natural immunity to the abnormal glycopeptides associated with cancer cells will be increased and immune surveillance will be increased for improved therapeutic effect. Similarly, when monoclonal antibodies specific for a combination epitope according to the invention are administered to an individual with reduced autoantibody levels but no detectable malignancy the increase in circulating antibody will provide increased immune surveillance for improved immunoprophylaxis.

Because ELISA methods for quantitation of autoantibodies, monoclonal antibodies and engineered antibodies in the circulation of an individual have been described, the results have been expressed herein in terms of absorbance units. It will be readily apparent to one skilled in the art that other known methods for quantitating antibodies may be substituted for ELISA. The corresponding ranges of normal and abnormal autoantibody levels as well as antibody levels monitored during treatment expressed in the units of measurement of such alternative assays can be determined using ordinary skill. The present invention is not limited to the use of ELISA or to absorbance for detection and quantitation, but contemplates all appropriate methods for detecting and quantitating antibody in the blood. For example, instead of absorbance units, one may determine the range of antibody titer that is indicative of normal or abnormal levels or monitor changes in antibody titer during treatment using methods known in the art.

Monoclonal antibodies specifically recognizing 23ST-glycosylation at T-15 of SEQ ID NO:4 may be prepared by immunizing mice, fusing immunized spleen cells with myeloma cells and screening the resulting hybridoma cells by ELISA, as is known in the art, using a glycopeptide containing the combination epitope as the immunogen, for example SEQ ID NO:4 (T15-23ST). An adjuvant such as KLH or tetanus toxoid may be conjugated to the glycopeptide to increase its immunogenicity, for example as described in *antibodies: A Laboratory Manual* (Ed Harlow and David Lane). Hybridomas will initially be selected and screened for reactivity with only SEQ ID NO:4 (T15-23ST) and not with other glycopeptides found in the MUC1 glycopeptide library that was originally used to isolate SEQ ID NO:4 (T15-23ST). The selected hybridomas will then be screened for production of monoclonal antibodies that react specifically with the T15-23ST combination epitope. That is, the selected hybridomas will be further screened and selected for monoclonal antibodies that recognize the combination epitope of SEQ ID NO:2 (T3-23ST) (i.e., both the glycoform and the peptide) with high specificity and affinity. The most preferred monoclonal antibody will react strongly with 23ST core 1 carbohydrate structures linked to T-15 of SEQ ID NO:4 or T-3 of SEQ ID NO:2 but will have substantially no reactivity with other core 1 structures (e.g., T, dST, 26ST), with Tn or STn, or with sialylated or unsialylated core 2 carbohydrate structures when they are present at T-15 of SEQ ID NO:4 or at T-3 of SEQ ID NO:2. Preferably, the specificity of the monoclonal antibody is such that cross-reactivity with non-target carbohydrate structures is 80% or less, preferably 50% or less, more preferably 20% or less, or most preferably 10% or less of reactivity with the immunogen glycopeptide (defined as 100% in conventional binding assays). In one embodiment, the monoclonal antibody directed against the SEQ ID NO:4 (T3-ST) combination epitope has binding specificity of 50% or less for combination epitopes in which T3 of SEQ ID NO:4 is linked to a carbohydrate structure comprising a substitution at the 6-position of GalNAc (e.g., NeuNAc or GlcNAc at the 6-position), and for Tn and T combination epitopes. For example, the desired monoclonal antibody may have binding specificity of 10% or less (such as <0.1-5%, <0.1-1%, or undetectable binding) to 6-substituted epitopes and binding specificity of 50% or less for Tn and T combination epitopes (such as 10-20%, <0.1-10%, <0.1-1%, or undetectable binding). The binding affinity of the selected monoclonal antibodies for the immunogen glycopeptides will preferably be 1500 nM or less in BIACORE assays (Kd) or 700 nM or less in ELISA assays (IC50). In a specific embodiment the binding affinity is less than 180 nM (Kd) or less than 100 nM (IC50). In a preferred embodiment the binding affinity is about 0.4 nM (Kd) or about 0.6 nM (IC50). Such monoclonal antibodies will be highly specific for the combination epitope that is the target of the protective autoantibodies described herein and will bind with high affinity. They will therefore be highly effective for treatment and prevention of cancers expressing MUC1 having the combination epitope.

Monoclonal antibodies specifically recognizing 23ST glycosylation at T-15 of SEQ ID NO:3 may be prepared in a similar manner and will similarly recognize the combination epitope of SEQ ID NO:3 (T15-23ST) (i.e., both the glycoform and the peptide) with high specificity and affinity. They will be selected to be specific for, and react strongly with, the 23ST structure at T-15 of SEQ ID NO:3 or T-3 of SEQ ID NO:1. The most preferred monoclonal antibody produced will exhibit substantially no reactivity with other core 1 carbohydrate structures (e.g., T, dST, 26ST), with Tn or STn, or with sialylated or unsialylated core 2 carbohydrate structures linked to T-15 of SEQ ID NO:3 or T-3 of SEQ ID NO:1. Preferably, the specificity of the monoclonal antibody is such that cross-reactivity with non-target carbohydrate structures is 80% or less, preferably 50% or less, more preferably 20% or less, or most preferably 10% or less of reactivity with the immunogen combination epitope (defined as 100% in conventional binding assays). In one embodiment, the monoclonal antibody directed against SEQ ID NO:4 (T3-ST) combination epitope has a binding specificity of 50% or less for combination epitopes in which T3 of SEQ ID NO:4 is linked to a carbohydrate structure comprising a substitution at the 6-position of GalNAc (NeuNAc or GlcNAc at the 6-position), and for Tn and T combination epitopes. For example, the desired monoclonal anatibody may have binding specificity of 10% or less (such as <0.1-5%, <0.1-1%, or undetectable binding to 6-substituted epitopes and binding specificity of 50% or less for Tn and T combination epitopes (such as 10-20%, <0.1-10%, <0.1-1%, or undetectable binding). The binding affinity of the selected monoclonal antibodies for the immunogen glycopeptides will preferably be 1500 nM or less in BIACORE assays (Kd) or 700 nM or less in ELISA assays (IC50). In a specific embodiment the binding affinity is less than 180 nM (Kd) or less than 100 nM (IC50). In a preferred embodiment the binding affinity is about 0.4 nM (Kd) or 0.6 nM (IC50). Such monoclonal antibodies will be highly specific for the combination epitope that is the target of the protective autoantibodies described herein and will bind the epitope with high affinity. They will therefore be highly effective for treatment and prevention of cancer expressing MUC1 having the combination epitope.

Alternatively, the serum autoantibodies directed against the combination epitopes SEQ ID NO:2 (T3-23ST) and/or SEQ ID NO:1 (T3-23ST) can be used to design specific engineered antibody therapeutics that are chemically or biologically synthesized (for example, using recombinant DNA methods). Such antibody therapeutics include, but are not limited to, antibody binding fragments such as Fab, $Fab_2$, Fv, scFv, minibodies, diabodies, triabodies and tetrabodies. Engineered antibodies provide substantial technical and therapeutic advantages over conventional mAbs because of their smaller size and because they are easily conjugated to active molecules such as drugs, toxins and radioisotopes for therapeutic use. In addition, engineered antibodies that are multivalent may be designed to react with both SEQ ID NO:1 (T3-23ST) and SEQ ID NO:2 (T3-23ST). The engineered antibodies will also be designed such that they react specifically with the combination epitope(s) of the invention and not with other glycopeptides found in the MUC1 glycopeptide library that was originally used to isolate SEQ ID NO:4 (T15-23ST) and SEQ ID NO:3 (T15-23ST). More specifically, such antibodies will have little or no reactivity with SEQ ID NO:4 or SEQ ID NO:3 when T-15 O-glycosylation other than 23ST is present. Further, the selected antibody will be designed to recognize the combination epitope of SEQ ID NO:2 (T3-23ST) and/or SEQ ID NO:1 (T3-23ST) (i.e., both the glycoform and the peptide) and will be similarly specific for the 23ST structure in these glycopeptides. That is, the preferred antibody designed in this manner will not react with sialylated or unsialylated core 2 structures or with Tn, T, dST, 26ST or STn core 1 carbohydrate structures when they are present at T-15 of SEQ ID NO:4 or at T-3 of SEQ ID NO:2 and/or when they are present at T-15 of SEQ ID NO:3 or at T-3 of SEQ ID NO:1. Such engineered antibody immunotherapeutics will be useful in the same therapeutic and immunoprophylactic methods and compositions as the monoclonal antibodies described above.

Immunotherapeutic and immunoprophylactic compositions comprising the monoclonal antibodies or engineered antibodies are also contemplated by the invention. In a preferred embodiment, the immunotherapeutic or immunoprophylactic antibody composition is a composition for treatment or prevention, respectively, of cancers which express the combination epitope of SEQ ID NO:1 (T3-23ST), SEQ ID NO:2 (T3-23ST), SEQ ID NO:3 (T15-23ST) or SEQ ID NO:4 (T15-23ST). In a specific aspect, the immunotherapeutic antibody composition is a composition for treatment of breast cancer, colon cancer or, renal cancer. The composition may comprise a monoclonal or engineered antibody as described above and at least one pharmaceutically acceptable excipient. For use in treating or preventing cancer, the composition will typically be in the form of an injectable composition such as a solution, suspension or emulsion incorporating the monoclonal or engineered antibody and a liquid excipient (e.g., saline, water, phosphate or carbonate buffer, propylene glycol, sorbitol, sucrose, etc.).

Therapeutic utility of the combination epitopes, peptides containing the combination epitopes and monoclonal or engineered antibodies directed to the combination epitopes for eliciting an immune response and for immunotherapy of cancer are confirmed in a murine MUC1 model accepted in the field for evaluation of immune response and immune tolerance to MUC1 and for evaluation of anti-MUC1 vaccine formulation in vivo within the context of an animal that expresses MUC1. See Rowse, G. J., et al. *Cancer Res.* 1998; 58:315-321. This mouse strain (MUC1.Tg) is transgenic for human MUC1 and is immune-tolerant to stimulation by MUC1 as evidenced by the ability of MUC1-expressing tumors to grow. It is therefore an appropriate preclinical model for evaluating anti-MUC1 immunotherapy formulations.

For confirmation of an in vivo immune response to the combination epitopes of the invention, glycopeptides containing the SEQ ID NO:1 (T3-23ST) or SEQ ID NO:2 (T3-23ST) epitopes are conjugated to an adjuvant peptide such as KLH and injected subcutaneously into MUC1.Tg mice in a solution with Freunds adjuvant (e.g., 10-15 µg glycopeptides in 200 µL total volume). Multiple immunizations (e.g., 4 injections 14 days apart) are administered and blood samples obtained following completion of the immunization schedule.

Post-immunization response is evaluated by ELISA generally as described by Sorensen, A. L., et al. *Glycobiology* 2006; 16(2):96-107, using the immunizing glycopeptides for capture of serum antibodies followed by detection of bound antibodies with labeled anti-mouse immunoglobulins (such as peroxidase-conjugated rabbit anti-mouse immunoglobulins). For isotyping, peroxidase-conjugated isotype-specific antibodies (such as goat anti-mouse IgM, IgG1, IgG2a, IgG2b or IgG3) are used as detection antibodies. Reactivity of induced antibodies with MUC1-expressing cancer cells is evaluated by incubating appropriate cell lines (for example, T47D which is reported to express at least some ST O-glycans) with immunized mouse sera in serial dilutions, followed by incubation with labeled anti-mouse immunoglobulins (such as FITC-conjugated rabbit anti-mouse immunoglobulins). Labeled cells are mounted on slides and examined under a fluorescence microscope to determine the extent of reaction of immune sera with MUC1 ST glycan epitopes on the cell surface.

The combination epitopes of the invention, either alone or contained in larger peptides as described above, are expected to overcome tolerance in MUC1.Tg mice and elicit a specific humoral immune response of sufficient strength to produce strong reactivity in the ELISA and immunocytochemistry assays described above. These results will provide a strong indication that peptides containing the combination epitopes SEQ ID NO:1 (T3-23ST) and/or SEQ ID NO:2 (T3-23ST) have utility as therapeutic vaccines for treatment of MUC1-expressing cancers in humans, in particular breast cancer, colon cancer and renal cancer.

As further evidence of the therapeutic utility of peptides containing the combination epitopes SEQ ID NO:1 (T3-23ST) and/or SEQ ID NO:2 (T3-23ST), anti-tumor response in the MUC1.Tg murine model is evaluated, generally as described by Mukherjee, P., et al. *Vaccine*. 2007; 25(9): 1607 1618. The host is injected subcutaneously with MUC1-expressing cancer cells (such as MC28 colon cancer cells transfected with MUC1 or a similar breast cancer cell line), typically in the flank, and the tumors are allowed to grow for a period of time, such as about 7 days, prior to immunization. Combination epitope-containing peptides in compositions with adjuvants (e.g., incomplete Freunds adjuvant) are administered subcutaneously at a site away from the tumor injection site. The immunization schedule is typically every seven days for 21 days, at which time the animals are sacrificed. Tumor size is measured with calipers daily during the immunization cycle and tumor weight in grams is calculated based on length and width of the tumor. An effect of immunization on tumor growth is evidenced by a slower rate of tumor growth in immunized mice as compared to unimmunized animals. Ideally, tumor growth is substantially completely prevented in immunized animals, that is, tumor growth is undetectable by palpation upon completion of the immunization protocol.

Highly immunotherapeutic peptides according to the invention will reduce tumor burden by at least 50% (either with or without the addition of adjuvants), preferably at least 70%, most preferably at least 90%. In some cases, complete prevention of tumor growth in MUC1.Tg mice may be achieved by immunotherapy using peptides containing the combination epitopes of the invention.

Polyclonal antibodies specific for the combination epitopes may also be generated using methods known in the art. Because the combination epitopes are strongly cancer-associated, such polyclonal antibodies will be useful for in vitro assays to determine the presence or absence of the disease, the prognosis of a cancer patient and an individual's level of risk for developing cancer. The monoclonal antibodies and engineered synthetic antibodies described above may also be used in similar assays for similar purposes.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A synthetic glycopeptide which consists of SEQ ID NO:3, wherein glycosylation consists of 23ST at T15 of SEQ ID NO:3, or which consists of SEQ ID NO:4, wherein glycosylation consists of 23ST at T15 of SEQ ID NO:4.

2. A pharmaceutical composition comprising the glycopeptide of claim 1 and a pharmaceutically acceptable excipient.

3. A method for treating MUC1-expressing cancer comprising administering the glycopeptide of claim 1 to a human cancer patient.

4. An in vitro method for detecting or quantifying an antibody in serum, wherein the antibody is an endogenous autoantibody or an exogenously administered antibody, the method comprising:

a) contacting a glycopeptide according to claim 1 with a serum sample under conditions sufficient to allow binding of the antibodies in the serum to the glycopeptide; and b) detecting or quantitating the binding of the antibodies in the serum sample with the glycopeptide, wherein the endogenous autoantibody or exogenously administered antibody binds specifically to a combination epitope defined by the 23ST glycosylation of the glycopeptide.

5. The method of claim 4, wherein the amount of serum antibody detected or quantitated is indicative of potential efficacy of immunotherapy using the glycopeptide.

6. The method of claim 4, wherein the amount of serum antibody detected or quantitated is indicative of potential efficacy of immunoprophylaxis or immunotherapy using the exogenously administered antibody.

7. The method of claim 4, wherein the amount of serum autoantibody detected or quantitated is used to identify individuals likely to benefit from administration of the glycopeptide, or a monoclonal or engineered antibody which specifically binds to a combination epitope defined by the 23ST glycosylation of the glycopeptide.

8. An in vitro method for evaluating or monitoring the efficacy of vaccine therapy comprising:
   a) contacting a glycopeptide according to claim 1 with a serum sample obtained from a patient immunized with a pharmaceutical composition comprising a vaccine glycopeptide, wherein the vaccine glycopeptide comprises SEQ ID NO:3, wherein glycosylation consists of 23ST at T15 of SEQ ID NO:3, and/or comprising SEQ ID NO:2, wherein glycosylation consists of 23ST at T3 of SEQ ID NO:2;
   b) quantitating the binding of autoantibodies in the serum sample with the glycopeptides of step (a), wherein the autoantibodies are specific to the glycopeptide; and
   c) determining if the amount of autoantibody is increased or decreased relative to a preselected baseline amount of autoantibody.

9. An in vitro method for evaluating the prognosis of a cancer patient having a MUC1-expressing cancer comprising:
   a) contacting a glycopeptide according to claim 1 with a serum sample obtained from the cancer patient under conditions sufficient to allow binding of autoantibodies in the serum to the glycopeptide;
   b) quantitating the binding of autoantibodies in the serum sample with the glycopeptide; and
   c) determining if the amount of autoantibody is increased or decreased relative to a preselected threshold amount indicative of cancer patient prognosis,
   wherein a decrease in the amount of autoantibody relative to the preselected threshold amount indicates poor prognosis.

10. A method for evaluating a risk for developing MUC1-expressing cancer in a human comprising:
    a) contacting a glycopeptide according to claim 1 with a human serum sample under conditions sufficient to allow binding of autoantibodies in the serum to the glycopeptide;
    b) quantitating autoantibodies in the serum sample; and
    c) detecting an increase or decrease in autoantibody level relative to a baseline as an indication of the risk of developing MUC1-expressing cancer,
    wherein a reduction in autoantibody level relative to the baseline indicates a risk for developing MUC1-expressing cancer.

11. A method for detecting cancer in a human comprising:
    a) contacting glycopeptide according to claim 1 with a human serum sample under conditions sufficient to allow binding of autoantibodies in the serum to the glycopeptide; and
    b) determining the level of autoantibodies in the serum sample; and
    c) comparing the autoantibody level with normal autoantibody levels as an indication of the presence of cancer,
    wherein a reduction in autoantibody level compared to normal antibody level indicates presence of cancer.

12. The method of claim 4, wherein quantitative binding of the autoantibodies is reduced compared to quantitative binding in normal human serum.

13. The method of claim 4, wherein autoantibody binding is quantitated by ELISA.

14. The method of claim 9, wherein autoantibody binding is quantitated by ELISA.

15. The method of claim 11, wherein the level of autoantibodies in the serum sample is determined by ELISA.

16. The method of claim 10, wherein the autoantibodies are quantitated by ELISA.

* * * * *

SEQUENCE LISTING

<160> NUMBER OF SEQ ID NOS: 4

<210> SEQ ID NO 1

```
<211> LENGTH: 7
<212> TYPE: PRT
<213> ORGANISM: Homo sapiens
<220> FEATURE:
<221> NAME/KEY: CARBOHYD
<222> LOCATION: (3)..(3)

<400> SEQUENCE: 1

Pro Asp Thr Arg Pro Ala Pro
1               5

<210> SEQ ID NO 2
<211> LENGTH: 4
<212> TYPE: PRT
<213> ORGANISM: Homo sapiens
<220> FEATURE:
<221> NAME/KEY: CARBOHYD
<222> LOCATION: (3)..(3)

<400> SEQUENCE: 2

Gly Ser Thr Ala
1

<210> SEQ ID NO 3
<211> LENGTH: 23
<212> TYPE: PRT
<213> ORGANISM: Homo sapiens
<220> FEATURE:
<221> NAME/KEY: CARBOHYD
<222> LOCATION: (15)..(15)

<400> SEQUENCE: 3

Ser Thr Ala Pro Pro Ala His Gly Val Thr Ser Ala Pro Asp Thr Arg
1               5                   10                  15

Pro Ala Pro Gly Ser Thr Ala
            20

<210> SEQ ID NO 4
<211> LENGTH: 23
<212> TYPE: PRT
<213> ORGANISM: Homo sapiens
<220> FEATURE:
<221> NAME/KEY: CARBOHYD
<222> LOCATION: (15)..(15)

<400> SEQUENCE: 4

Gly Val Thr Ser Ala Pro Asp Thr Arg Pro Ala Pro Gly Ser Thr Ala
1               5                   10                  15

Pro Pro Ala His Gly Val Thr
            20
```